US008679796B2

(12) United States Patent
Carvalho Fernandes De Miranda Reis et al.

(10) Patent No.: US 8,679,796 B2
(45) Date of Patent: Mar. 25, 2014

(54) GALACTOSE-RICH POLYSACCHARIDE, PROCESS FOR THE PRODUCTION OF THE POLYMER AND ITS APPLICATIONS

(75) Inventors: Maria D'ascenção Carvalho Fernandes De Miranda Reis, Lisbon (PT); Rui Manuel Freitas Oliveira, Costa da Caparica (PT); Cristina Paula Pereira Da Cunha Rodrigues Oliveira, Costa da Caparica (PT); Maria Filomena Andrade De Freitas, Pinhal Novo (PT); Victor Manuel Delgado Alves, Almada (PT); Joana Oliveira Pais, Monte de Caparica (PT)

(73) Assignee: 73100-Setenta e Tres Mil e Cem, Lda., Vila Real (PT)

( * ) Notice: Subject to any disclaimer, the term of this patent is extended or adjusted under 35 U.S.C. 154(b) by 911 days.

(21) Appl. No.: 12/595,392

(22) PCT Filed: Apr. 9, 2008

(86) PCT No.: PCT/PT2008/000015
§ 371 (c)(1),
(2), (4) Date: Nov. 9, 2009

(87) PCT Pub. No.: WO2008/127134
PCT Pub. Date: Oct. 23, 2008

(65) Prior Publication Data
US 2010/0113765 A1    May 6, 2010

(30) Foreign Application Priority Data

Apr. 11, 2007 (PT) .......................................... 103714

(51) Int. Cl.
*C12P 19/04* (2006.01)
(52) U.S. Cl.
USPC ............................................................ 435/101
(58) Field of Classification Search
None
See application file for complete search history.

(56) References Cited

U.S. PATENT DOCUMENTS 4,948,785 A    8/1990    Nguyen

FOREIGN PATENT DOCUMENTS

| EP | 0 410 604 A1 | 1/1991 |
| FR | 2 617 848 A | 1/1989 |

OTHER PUBLICATIONS

Fischer et al., Effect of root exudates on the exopolysaccharide composition and the lipopolysaccharide profile of *Azospirillum brasilense* Cd under saline stress, 2003, FEMS Microbiology Letters 219: 53-62.*
Brandl et al.,*Pseudomonas oleovorans* as a Source of Poly(β-Hydroxyalkanoates) for Potential Applications as Biodegradable Polyesters, 1988, Appl. Environ. Microbiol. 54(8): 1977-1982.*
Williams et al., Preliminary studies on the composition and rheological properties of the extracellular polysaccharide synthesized by *Pseudomonas* PB1 (NCIB 11264), Biochimica et Biophysica Acta (BBA)—General Subjects, 1979, 585(4): 611-619.*
Williams et al., Exopolysaccharide production by *Pseudomonas* NCIB11264 grown in continuous culture, 1978, Journal of general microbiology 104(1): 47-57.*
"Synthesis of short-/Medium-Chain-Length Poly (hydroxyalkanoate) Blends by Mixed Culture Fermentation of Glycerol" Richard D. Ashby et al.; XP-002487059; vol. 6, No. 4, 2005, pp. 2106-2112.
International Search Report and Written Opinion of the International Searching Authority for PCT Patent App. No. PCT/PT2008/000015 (Sep. 17, 2008).
Egorov et al. "New strain of methylotrophic bacteria *Pseudomonas oleovorans*—a polysaccharide producer" Prikl Biokhim Mikrobiol. Jul.-Aug. 1976; 12(4):524-7 (English Language Abstract provided).

\* cited by examiner

*Primary Examiner* — Jon P Weber
*Assistant Examiner* — Robert Yamasaki
(74) *Attorney, Agent, or Firm* — Gary J. Gershik; Cooper & Dunham LLP

(57) ABSTRACT

This invention concerns a biopolymer consisting of a polysaccharide composed of galactose (50-90%), glucose (1-25%), mannose (1-25%) and rhamnose (0.5-20%), which may additionally contain, in trace amounts, xylose, fucose, ribose, arabinose and/or fructose. The galactose-rich polymer also contains non-saccharide components, namely, acyl groups. This invention also concerns a process for the production of the galactose-rich polymer, by microbial fermentation using glycerol or glycerol-rich substrates as carbon source, and recovery of the polymer from the culture broth. From the process for the production of the galactose-rich polymer results the co-production of intracellular biopolymers, namely, polyhydroxyalkanoates. This invention also concerns to the application of the galactose-rich polymer and the products of its partial or complete degradation and/or derivatization, namely, galacto-oligosaccharides, galactose, rhamnose and others, by physical, chemical and/or biological methods, in food, agricultural, textile and paper industries, pharmaceutical and cosmetic products, oil and metal recovery in mining industry, industrial waste treatment and wastewater treatment, among others.

16 Claims, 3 Drawing Sheets

Figure 1:
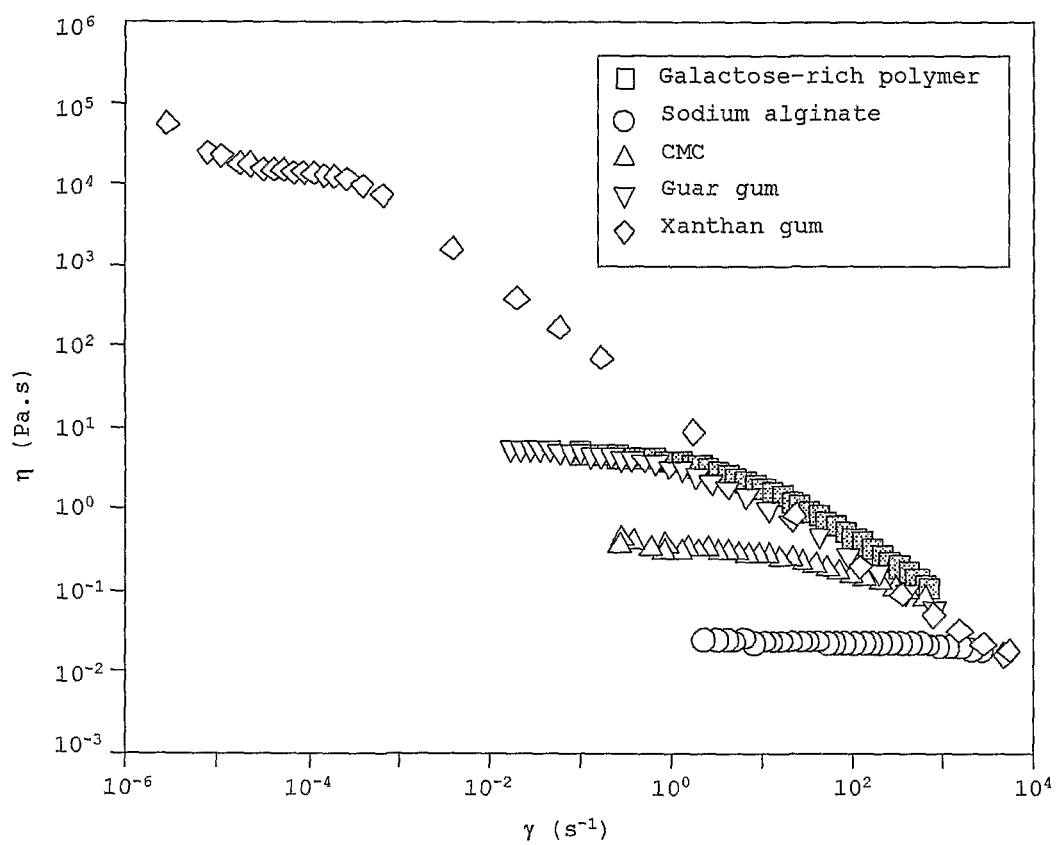

GALACTOSE-RICH POLYSACCHARIDE, PROCESS FOR THE PRODUCTION OF THE POLYMER AND ITS APPLICATIONS

This application is a U.S. national phase filing under 35 U.S.C. §371 of PCT Application No. PCT/PT2008/000015, filed Apr. 9, 2008, and claims priority thereto under 35 U.S.C. §119 to Portuguese patent application no. 103714, filed Apr. 11, 2007, the entireties of both of which are incorporated by reference herein.

FIELD OF INVENTION

This invention relates to a biopolymer consisting of a polysaccharide composed of galactose (50-90%), glucose (1-250), mannose (1-25%) and rhamnose (0.5-20%), which may additionally contain, in trace amounts, other neutral sugars, such as xylose, fucose, ribose, arabinose and/or fructose, and non-saccharide components, such as acyl groups, the process for the production of the galactose-rich polymer by microbial fermentation, preferably using glycerol or glycerol-rich substrates as carbon source, and the application of the galactose-rich polymer and products thereof, in food, agricultural, textile and paper industries, in pharmaceutical and cosmetic products, for oil and metal recovery in the mining industry, in wastewater treatment, among others.

BACKGROUND OF THE INVENTION

Polysaccharides are high molecular weight carbohydrates, composed by one or more monosaccharides that form repeating units and polymerize. They are the most abundant macromolecules among living organisms, being present in all plants and algae, in several animals and in some microorganisms. Due to their physical-chemical properties, namely, their water retention capacity, film forming and rheology (viscosity, gelling, emulsifying, etc.), polysaccharides are largely used in a wide variety of industrial applications.

Currently, polysaccharides obtained from plants (ex. Guar gum, Arabic gum, pectins), algae (ex. alginates, carrageenan, agar) or crustaceous (ex. chitin) dominate the biopolymers market, where microbial polysaccharides still represent a small fraction. The main factors limiting microbial polysaccharide wider use are associated with their production costs, mainly substrate cost, and also to the fact that many of the producing strains are pathogenic or it is difficult to obtain public acceptance for some applications. Nevertheless, during the last years, there has been an increasing interest in isolating and identifying new microbial polysaccharides that may compete with traditional polysaccharides due to their physical-chemical properties and rheology. The production of plant and algal polysaccharides, in particular, is subjected to climatic and environmental impact, such as pollution, that cause great variability both in the quantity and the quality of the polymers obtained. On the other hand, many microbial polysaccharides are characterized by a variety of properties not found in plant polymers, such as, for example, anti-tumor, antiviral, anti-inflammatory or immune-stimulating activities.

Microbial polysaccharides that have been extensively studied and are currently being commercially exploited include: bacterial cellulose, produced by *Acetobacter xylinum*, whose properties are similar to plant cellulose; dextran, produced by bacteria of the *Leuconostoc* genus, and levan, produced by bacteria of the genera *Bacillus*, *Zymomonas* and *Lactobacillus*, which are exclusively bacterial products; xanthan, produced by bacteria of the *Xanthomonas* genus, and gellan gum, produced by *Sphingomonas paucimobilis*, which have improved physical properties compared to traditional polysaccharides, such as alginate or carrageenan; hyaluronic acid, produced by *Streptococcus equii*, and succinoglycan, produced by bacteria of the genera *Pseudomonas*, *Rhizobium*, *Agrobacterium* and *Alcaligenes* that find medical, pharmaceutical and cosmetic applications due to their similarity to eukaryotic polymers.

Due to the growing interest in renewable resources as alternatives to chemical products, the search for new products will certainly be intensified and new microbial polysaccharides with commercial interest are likely to arise. The commercial value of a polysaccharide will depend on its composition, on the amount produced and the ease of extraction and processing. The industrial development will depend on its rheological properties, namely its ability to form viscous solutions, stability for wide temperature and pH ranges, and on its unique biological properties and/or the fact that they may be used in new applications.

Galactose-rich polymers may be included among the polysaccharides with potential industrial interest. These polymers may be found in plants (ex. Arabic gum), algae (ex. carrageenan and agar) and in several microorganisms, including protozoa, fungi, yeast and bacteria. The presence of galactose residues in microbial polymers is rather common, even though the type of glycosyl linkage involved varies. These polysaccharides may be homopolymers of galactose (galactans) or heteropolymers containing, besides variable amounts of galactose, other sugar residues, most commonly glucose, mannose, rhamnose, arabinose and/or fucose. Many of these polymers contain, besides neutral sugars, acidic sugars (ex. glucuronic acid, galacturonic acid) or amino-sugars (ex. N-acetyl-glucosamine, N-acetyl-galactosamine). The presence of non-sugar components, such as acyl groups (ex. acetate esters, pyruvate ketals, succinyl half esters) or inorganic residues (ex. sulphate, phosphate) is also quite common.

Galactose homopolymers are produced by bacteria such as *Bifidobacterium infantis* (Tone-Shimokawa et al., 1996), *Bifidobacterium catenulatum* (Nagaoka et al., 1996), *Klebsiella pneumoniae* (Whitfield at al., 1991), *Pasteurella haemolytica* (Lacroix et al., 1993), *Serratia marcescens* (Aucken et al., 1998), *Azorhizobium caulinodans* (D'Haeze at al., 2004) and *Methylobacterium* sp. VTT-E-11929 (Verhoef et al., 2003).

The main component of the polymer of the invention is a heteropolysaccharide, containing besides galactose as its main component, other neutral sugars, namely, glucose, mannose and rhamnose, which confer it a higher structural complexity. Unlike the galactans produced by *Bifidobacterium infantis* and *Bifidobacterium* catenulatum, wherein the galactose residues are present in the form of furanose rings, the polysaccharide of this invention contains all galactose residues in the form of pyranose rings. On the other hand, the extraction process of the referred galactans is rather difficult since they are cell wall components, whereas the extraction of the polymer of the invention is much easier because it is an extracellular product. The galactans produced by *Klebsiella pneumoniae*, *Pasteurella haemolytica* and *Serratia marcescens* are lipopolysaccharides, composed by alternate pyranose and furanose rings of galactose. These bacteria are pathogenic for Man (*K. pneumoniae* and *S. marcescens*) and animals (*P. haemolytica*), being the galactans produced by them associated with their infection development.

For this reason, the interest in these polymers is restricted to the study of the pathogenesis of the infections caused by the producing bacteria, being their commercial development unlikely. Besides, taken that they are lipopolysaccharides, the extraction and purification process is more difficult than for the extracellular polymer of the invention.

Heteropolymers containing galactose as their main component are produced by a wide group of microorganisms, namely, bacteria of the genera *Bifidobacterium, Klebsiella, Erwinia, Methylobacterium, Pseudomonas, Lactobacillus, Alcaligenes* and *Streptococcus*.

Rhamnogalactans (polysaccharides composed by galactose and rhamnose) are common cell wall components of bacteria of the *Bifidobacterium* genus. An example of this is the cell wall polysaccharide of *Bifidobacterium longum* that is composed by galactose (about 60%) and rhamnose (about 40%), both in the form of pyranose rings (Nagaoka et al., 1995). The polymer of the invention, besides its extracellular nature, differs from the *Bifidobacterium longum* polymer by having a lower percentage of rhamnose and also by having other neutral sugars (glucose and mannose).

Some bacteria of the *Klebsiella* genus produce galactose-rich extracellular heteropolymers such as: *Klebsiella* sp. strain K32 that produces a polysaccharide composed of galactose (45-63%) and rhamnose (12-55%), with a variable pyruvate content (Bryan et al., 1986); *Klebsiella* sp. S11 that produces a polysaccharide composed of galactose (62.5%), glucose (25%) and mannose (12.5%), with a minor content of uronic acids (Dermlim et al., 1999); and *Klebsiella planticola* DSM 3092 that produces a polysaccharide composed of galactose (38.2%), mannose (15.9%), glucose (1.7%), glucuronic acid (17.5%), acetate (5.3%), succinate (2.6%) and sulphate (14.6%) (EP0184755). The polymer of the invention differs from these polysaccharides by its composition, namely, the simultaneous presence of galactose, glucose, mannose and rhamnose, and the absence of uronic acids, which distinguishes it from the polysaccharide produced by *Klebsiella planticola*.

The production of galactose-rich heteropolymers also occurs in bacteria of the *Methylobacterium* genus. An example is the extracellular polysaccharide methylan, produced by *Methylobacterium organophilum*, composed by galactose, glucose and mannose (in the molar ratio 4:3:3), acyl groups (pyruvate and acetate) and uronic acids (U.S. Pat. No. 5,064,759). The polymer of the invention differs from methylan polysaccharide by its higher galactose content and by the absence of uronic acids.

Among the phytopathogenic bacteria of the *Erwinia* genus, some produce galactose-rich polysaccharides. Examples thereof include: *Erwinia amylovora* produces amylovoran, an extracellular polysaccharide composed by galactose (about 80%) and glucuronic acid (about 20%), acyl groups (acetate and pyruvate) and traces of glucose (Eastgate et al., 2000); *Erwinia pyrifoliae* produces an extracellular polysaccharide, similar to amylovoran, but with a higher acetate content and without glucose (Kim et al., 2002); *Erwinia stewartii (Pantoea stewartii* ssp. *stewartii)* produces stewartan, a capsular polysaccharide similar to amylovoran but with a higher glucose content (Minogue et al., 2005); *Erwinia chrysanthemi* Ech6 produces an extracellular polysaccharide composed by galactose and fucose, in equal amounts, glucose and glucuronic acid (Yang et al., 2001). The polymer of the invention differs from these polymers by the fact that it does not contain glucuronic acid and, also, by its mannose and rhamnose contents.

Several *Enterobacter* species (ex. *Enterobacter amnigenus, Enterobacter cloacae*) produce heteropolysaccharides rich in galactose (21-24%) and fucose (16-27%), containing variable amounts of glucose, mannose and rhamnose, acyl groups (acetate and pyruvate) and uronic acids (glucuronic acid and/or galacturonic acid) (Verhoef et al., 2005). Colanic acid, which is composed by galactose, fucose, glucose and glucuronic acid, is a typical extracellular polysaccharide produced by bacteria of the *Enterobacter* genus (Ratto et al., 2006). The polymer of the invention differs from these polysaccharides by its higher galactose content, trace or null fucose content and the absence of uronic acids.

The production of galactose-rich heteropolysaccharides also occurs in bacteria of the *Vibrio* genus, such as, for example, *Vibrio harveyi*, that produces a polysaccharide whose main components are galactose and glucose, with minor amounts of rhamnose, fucose, ribose, arabinose, xylose and mannose (Bramhachari et al., 2006). This polysaccharide also has a high content of uronic acids, namely, galacturonic acid that distinguishes it from the polymer of the invention.

Bacteria from the *Alcaligenes* genus, namely the strain *Alcaligenes* ATCC 31961, were referred as having the ability of producing a polysaccharide containing typically glucose and rhamnose, but also glucuronic, galactose, mannose, arabinose, fucose and ribose (EP0471597A1). The polymer of the invention differs from that, since it does not contain uronic acids.

Several lactic acid bacteria from the genera *Lactobacillus, Lactococcus* and *Streptococcus* produce a wide variety of heteropolysaccharides whose main components are galactose and glucose. These species include: *Lactobacillus delbrueckii* that produces several polysaccharides containing, besides galactose and glucose, rhamnose or mannose; *Lactobacillus rhamnosus* and *Lactobacillus kefuranofaciens* that produce polysaccharides containing galactose and glucose; *Lactobacillus paracasei* that produces a polysaccharide containing galactose and N-acetyl-galactosamine (Faber et al., 2001; Vanhaverbeke et al., 1998; Yang, 2000); *Lactococcus lactis* ssp. *cremoris* that produces polysaccharides composed by galactose and glucose or composed by galactose, glucose and rhamnose (Yang, 2000); *Streptococcus* species that produce several polysaccharides containing galactose and glucose, rhamnose, mannose or N-acetyl-galactosamine (Yang, 2000); *Streptococcus thermophilus* produces polysaccharides containing galactose and rhamnose (Vaninggelgem et al, 2004) or polysaccharides containing galactose, rhamnose and glucose (U.S. Pat. No. 5,965,127).

The production of galactose-rich polysaccharides also occurs in bacteria of the *Pseudomonas* genus, such as, for example: *Pseudomonas marginalis* that produces marginalan, an extracellular polysaccharide composed by galactose and glucose in equal molar amounts (Osman et al., 1989); *Pseudomonas fluorescens* that produces an extracellular polysaccharide whose main components are galactose, mannose and arabinose (Hung et al., 2005); *Pseudomonas paucimobilis* that produces a polysaccharide containing typically glucose and rhamnose, but also glucuronic, galactose, mannose, arabinose, fucose and ribose (EP0471597); and *Pseudomonas* species ATCC 53923 that produces a polysaccharide containing mannose, galactose and glucose in a molar ratio of 1.3:1.0:1.3, 10-25% uronic acids and 10-15% acetate (EP0410604). The polymer of the invention differs from marginalan because it contains, besides galactose and glucose, also mannose and rhamnose, as main components. The presence of arabinose in the polysaccharide produced by *Pseudomonas fluorescens* distinguishes it from the polysaccharide of the invention, in which arabinose is absent or is present in trace amounts. The polymer of the invention also differs from those produced by *Pseudomonas paucimobilis* and *Pseudomonas* species ATCC 53923 mainly because they do not contain uronic acids.

The polymer of the invention has a composition that distinguishes it from other galactose-rich polysaccharides from microbial origin, namely, because it has, besides galactose as the main sugar component, the neutral sugars glucose, mannose and rhamnose, further lacking uronic acids and amino-sugars.

The polymer of the invention is an extracellular product, which makes its extraction a relatively easy process, comparing to some of the polysaccharides that are constituents of the bacterial cell-wall or the plant or algae cell-walls.

Due to its biodegradability, the galactose-rich polymer does not cause any environmental problems. The polysaccharide of the invention has interesting rheological properties, namely, its behavior as a pseudoplastic fluid and its ability to form aqueous solutions with excellent viscosity, stable for wide pH and temperature ranges.

Although both the composition and the amount of polysaccharide produced by a microorganism are genetically determined traits, it is possible to influence both by altering the culture conditions. Polysaccharide production may be induced as part of a stress response, being generally favored by: presence of carbon source in excess, concomitant with limitation by another nutrient (ex. nitrogen or phosphorus); low temperatures; microaerophilic or anaerobic conditions or excessive aeration; saline stress; presence of cations (ex. $Ca^{2+}$ or $Sr^{2+}$); or the presence of toxic compounds or microbial growth inhibitors (ex. antibiotics or $H_2O_2$). The amount of polysaccharide produced is influenced by the medium composition and the incubation conditions, especially, the carbon availability, both intra and extracellular, and the ratio between carbon and other nutrients.

Most fermentation processes for the production of extracellular microbial polysaccharides are performed with pure cultures (ex. EP0410604, ES8701838, US2004/0197877). Nevertheless, it is possible to use mixed cultures of two or more microorganisms of which at least one is able to produce the polymer of interest. An example of this is the production of extracellular polysaccharides by a mixed culture of *Pseudomonas maltophilia* DSM 2130 and *Agrobacterium tumefaciens* DSM 2128 (U.S. Pat. No. 4,567,140).

Microbial polysaccharide production is usually performed by aerobic fermentation, being sugars (ex. glucose, sucrose, starch) the most commonly used carbon sources. Most processes described above for microbial galactose-rich polysaccharides used sugars as carbon sources, mainly glucose, or, in some cases, sucrose or lactose. For methylan production, by *Methylobacterium organophilum*, methanol was used as carbon source, or alternatively, mixtures containing methanol and glucose, mannose, galactose or succinate. The process of the present invention uses glycerol or glycerol-rich substrates as carbon source for the microbial fermentation. The use of glycerol is advantageous since it allows for the valorization of glycerol wastes (ex. glycerol-rich product from the biodiesel production), thus reducing the production costs associated with carbon source. The process of the invention also considers the use of other carbon sources (ex. sugars, methanol) as alternatives to glycerol or mixture thereof, which makes the process much more versatile.

In an aerobic fermentation, in which the culture broth viscosity continuously increases, reaching a highly viscous state, one of the main difficulties of the process is maintaining an efficient distribution of oxygen and nutrients across the broth. This is, frequently, achieved by keeping high aeration rates and/or high stirring rates. On the other hand, viscosity reduction to enhance mass transfer and polymer recovery may be achieved by adding nucleases to cell lysates or using engineered microbial strains that produce those enzymes. In fact, bacteria such as *Ralstonia eutropha, Methylobacterium organophilum, Aeromonas caviae, Azotobacter vinelandii, Alcaligenes latus, Escherichia coli* and *Klebsiella*, as well as some from *Pseudomonas* genus, have been genetically manipulated to produce nucleases during the production of polyhydroxyalkanoates and polysaccharides (WO 99/50389). The process differs from that of this invention in the type of polysaccharide produced and the carbon source used. In the process of this invention, the production of the galactose-rich polymer is performed with low dissolved oxygen concentrations, allowing for the minimization of aeration and, subsequently, reduction of operation costs.

The co-production of extracellular polysaccharides and intracellular biopolymers, namely, polyhydroxyalkanoates (PHA), occurs naturally in several microorganisms, under specific growth conditions. Examples of microorganisms capable of simultaneously producing polysaccharides and PHA, include: bacteria of the *Rhizobium* genus (ex. *Rhizobium meliloti*), that accumulate intracellular reserves of polyhydroxybutyrate (PHB), and produce an extracellular polysaccharide composed by glucose, galactose and glucuronic acid (Tavernier et al., 1997); the bacteria *Azotobacter vinelandii* and *Pseudomonas aeruginosa* that produce an extracellular polysaccharide, alginate, and accumulate intracellular PHB (Galindo et al., 2007; Pham et al., 2004). The process of the present invention may be used for the production of intracellular biopolymers, namely PHA, simultaneously with the production of the galactose-rich extracellular polymer.

The recovery of extracellular microbial polysaccharides usually involves the separation of the cells, following the precipitation of the polymer by the addition of a solvent miscible with water in which the polymer is insoluble (ex. EP0410604). Depending on the intended use for the polymer, it may be further subjected to additional processes for purification. On the other hand, there are some applications for which there is no need for a high degree of purity and the polymer may be used directly from the culture broth (ex. US2006/0147582).

Polysaccharides are used in a large range of applications, such as in medicine and food, pharmaceutical and chemical industries (US0197877A1).

In food industry, galactose-rich polysaccharides may be applied as thickening, binding, gelling, texturing, emulsifying and stabilizing agents in liquid systems, such as salad dressings, vinegar, ice-cream, ketchup, mustard, dehydrated products (ex. soups, sauces, cereals and pap meals) and meat-based products (ex. sausages). In the pharmaceutical industry, they have been used as binding agents and for drug controlled release.

Some microbial polysaccharides present flocculating activity, and may be used alone or mixed with other biopolymers, such as chitin derivates, galactomannans, glucomannans, alginates and starches (EP0471597A1). Flocculating agents are useful in colloid and cell aggregation, being currently used in industrial applications, such as water treatment and food and mining industries. Inorganic and synthetic organic flocculating agents are inexpensive products, but have a low biodegradability. On the other hand, some of them are dangerous for human health, namely polyacrilamides, whose monomers are neurotoxic, and poly(aluminium chloride) that induces Alzheimer disease. Although natural flocculating agents usually have a lower flocculating activity, they are safe and biodegradable, and its application will certainly increase in the near future.

A large percentage of the polymeric compounds produced by microorganisms, like polysaccharides, have the capacity of immobilizing toxic metals. This ability depends on the chemical composition and molecular structure of the biopolymer. Bacterial polysaccharides, such as alginate and xanthan gum, are able to immobilize actinides (ex. plutonium) forming erosion resistant aggregates. The use of microbial polysaccharides for toxic metal removal from contaminated soil and water has a great potential, and the interest in its application has been increasing.

The galactose-rich polysaccharides, namely Guar gum, are currently used in other areas, such as: paper industry, for paper properties enhancement (paper strength and surface improvement for printing); explosives, as binding agent in blasting slurries and water proofing agent in stick explosives (ex. ammonium nitrate, nitro-glycerine); petroleum industry, as suspending agent in well drilling; hydromulching, incorporated in the tackifier portion of the slurry used; and textile industry, as thickener for die.

Due to their biodegradability, polysaccharides have also found application in the preparation of films for packaging. Biopolymers, such as alginate, chitosan, starch, gellan and pectin, have been used in the development of biodegradable films for food packaging, since they present a low permeability to gases (carbon dioxide and oxygen).

The galactose-rich polysaccharides can also be converted into oligosaccharides (polymers that contain from 2 to 10 monomers) that may be used in the food industry. The interest in using these natural compounds as prebiotics (non-carcinogenic, non-digestible and low caloric compounds that stimulate the development of benefic microflora in the digestive tract) has been increasing, as traditional food additives are becoming less popular among consumers. Nowadays, the best strategy to obtain oligosaccharides in large quantities is based on the degradation of polysaccharides using physical treatments (microwave, heating, radiation, sonication), chemical treatments (acid hydrolysis), enzymatic reactions (using microbial enzymes) or by the action of specific microorganisms.

GENERAL DESCRIPTION OF THE INVENTION

The present invention concerns a biopolymer, whose main component is a high molecular weight polysaccharide, composed by galactose, glucose, mannose and rhamnose. The polysaccharide may, additionally, contain xylose, fucose, ribose, arabinose and/or fructose, in trace amounts, and non-sugar components, such as acyl groups. The polymer of the invention is insoluble in organic solvents and forms highly viscous aqueous solutions, with pseudoplastic fluid behavior. The viscosity of the polymer in aqueous solution is stable for a pH range of 3-10, decreasing as the temperature increases from 0° C. to 100° C. The polymer of the invention has both flocculating and emulsifying activities, and film-forming capacity.

The present invention also describes a process for the production of the galactose-rich polymer, by microbial fermentation, using glycerol or glycerol-rich substrates as carbon sources, in an aerated and stirred bioreactor. The process according to the invention also foresees the use of other carbon sources (ex. sugars, alcohols, organic acids or alkanes), as alternatives to glycerol or in mixtures with glycerol. The process of the invention further foresees the use of food or industrial waste, such as, for example, glycerol-rich product from biodiesel production, whey or olive-oil production wastes.

The microbial culture used in the fermentation process of this invention is a bacterium, for example, from the genera *Pseudomonas, Klebsiella, Methylobacterium, Erwinia, Alcaligenes, Lactobacillus, Streptococcus* or *Ralstonia*. The microbial culture is preferably a *Pseudomonas oleovorans* strain. The microbial culture is a wild type microorganism, a variant or a mutant, as long as it is able to produce the galactose-rich polymer. It is possible to use a pure culture or a mixed culture of several microorganisms, among which, at least one is capable of producing the galactose-rich polymer.

The fermentation process used for the production of the galactose-rich polymer consists of growing a microbial culture in an aerated aqueous nutrient medium. The fermentation starts with a high dissolved oxygen concentration, but, concomitantly with cellular growth, it is gradually reduced, being controlled below 30%, preferably, below 10% or null. The galactose-rich polymer is produced under conditions of nitrogen limitation and carbon availability, simultaneously with the maintenance of a low dissolved oxygen concentration.

The present invention describes the recovery of the galactose-rich polymer at the end of the fermentation, by the direct use of the culture broth, after a drying process. The present invention also describes the process for the extraction of the galactose-rich polymer in its native form, just as well as its purification process. The process of extraction of the polymer of this invention consists of cell removal by centrifugation of the culture broth, following the precipitation of the polymer by addition of a precipitating agent (ex. ethanol, acetone). The purification of the polymer involves the use of one or more additional processes (ex. dialysis, ultrafiltration or diafiltration of aqueous solution of the polymer).

This invention also concerns the use of the galactose-rich polymer in several food and industrial applications (ex. pharmaceutical, mining, paper, textile, explosive, etc.) and its use as a source of oligosaccharides and in the preparation of biodegradable films.

FIGURES

FIG. 1—Shear rate dependent viscosities of solutions of commercial Xanthan (◇), guar gum (∇), carboxymethyl cellulose (Δ), alginate (○) and galactose-rich polymer (■) measured during steady stress sweep tests, for a concentration of 0.01 g/ml, in 0.1M NaCl at 20° C.

Figure 2:
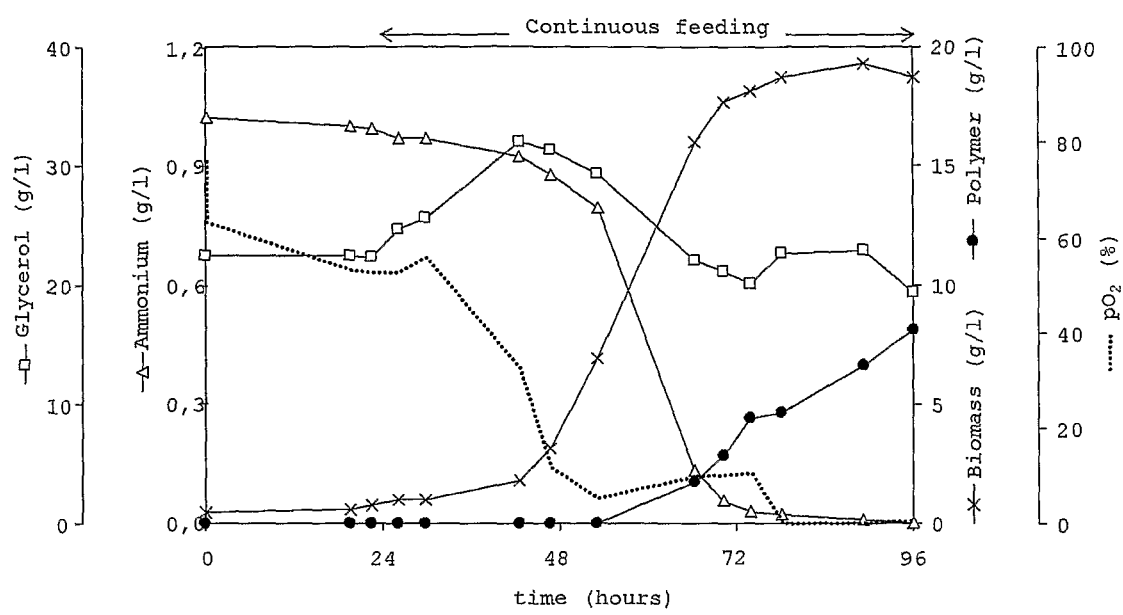

FIG. 2—Represents the time course of the consumption of the carbon source (glycerol) and nitrogen source (ammonium), the production of biomass and native polymer, during the fermentation process for the production of the polymer of the invention. Glycerol and ammonium are fed continuously to the bioreactor, after 20 hours of fermentation.

Figure 3:
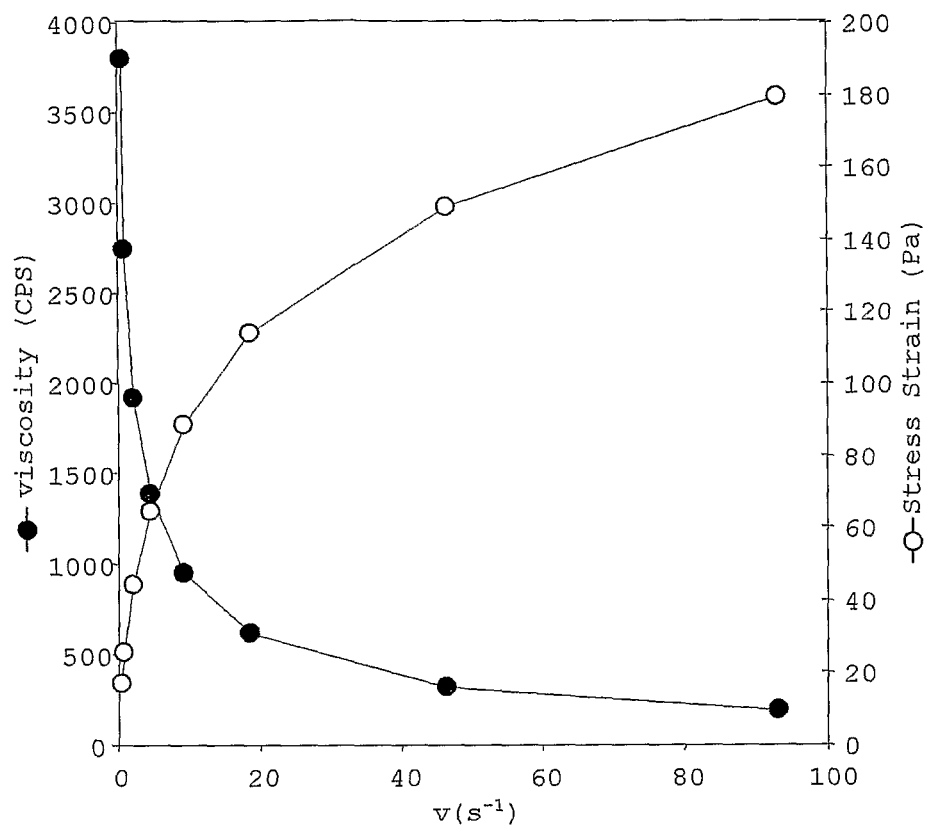

FIG. 3—Represents the rheological properties (viscosity and stress strain vs shear rate) of the culture broth at 96 h of fermentation.

DETAILED DESCRIPTION OF THE INVENTION

The present invention provides a galactose-rich polymer characterized in that it consists of galactose (50-90%), glucose (1-25%), mannose (1-25%) and rhamnose (0.5-20%), which may additionally contain, in trace amounts, xylose, ribose, fucose, arabinose and/or fructose, and nonsugar components, namely, acyl groups.

The present invention also provides a process for the production of the galactose-rich polymer, wherein the galactose-rich polymer is obtained by microbial fermentation using glycerol or glycerol-rich substrates as a carbon source.

In an embodiment, the microorganism is preferably a bacterium, preferably, belonging to the *Pseudomonas* genus, preferably, a strain of *Pseudomonas oleovorans*.

In an embodiment, the microorganism is a variant or a mutant of the referred microorganisms.

In an embodiment, a pure culture or a mixed culture comprising several microorganisms, among which at least one of the microorganisms is present.

In an embodiment, the process is characterized by comprising the following steps:
a. inoculating a microbial culture on an aqueous nutrient medium, having a carbon source, a nitrogen source and inorganic salts, aerated to maintain a dissolved oxygen concentration equal or higher than 80%, at a temperature between 5 and 75° C., preferably, between 26 and 37° C., and pH between 4.0 and 9.0, preferably between 6.0 and 7.5;
b. supplying the culture with a feeding solution consisting of an aqueous nutrient medium comprising a carbon source and inorganic salts, with or without a nitrogen source, when the dissolved oxygen concentration in the culture broth reaches a level below 50%, thus keeping the carbon source at a concentration between 10 and 100 g/L, preferably, between 10 and 20 g/L, and the nitrogen source exhausted or at a concentration below 0.3 g/L;
c. controlling the dissolved oxygen concentration in the culture broth in the bioreactor at a level below 30%, preferably, below 10% or null, and, simultaneously, keeping the carbon source at a concentration between 10 and 100 g/L, preferably, between 10 and 20 g/L, and the nitrogen source exhausted or at a concentration below 0.3 g/L.

In an embodiment, the carbon source is glycerol or glycerol-rich substrates or, alternatively, consisting of at least one of the following compounds, mixtures thereof or mixtures thereof with glycerol:
a. a monomeric, dimeric or olygomeric sugar, preferably glucose, fructose, sucrose or lactose;
b. an alcohol, preferably methanol;
c. an organic acid, preferably citrate, acetate, lactate or octanoate;
d. an alkane, preferably hexane or octane;

In an embodiment, the carbon source is a food or industrial waste comprising one or several of the compounds referred to above, such as molasses, glycerol-rich product from the biodiesel production, whey or olive-oil production wastes.

In an embodiment, the nitrogen source is an inorganic salt, an organic nitrogen compound or mixtures thereof.

In an embodiment, the nitrogen source is a food or industrial waste containing nitrogen compounds, such as, for example, soya flour, yeast extract, wheat bran or urea.

In an embodiment, the polymer is directly recovered from the culture broth, by drying or freeze drying, or alternatively being extracted by a process that consists of sequentially subjecting the culture broth to the following steps:
a. removing microbial cells from the culture broth, preferably by centrifugation, filtration, sedimentation or hydrocycles;
b. precipitating the polysaccharide by the addition of a polar solvent, preferably, acetone, ethanol or propanol;
c. separating the precipitated polymer, preferably by centrifugation or filtration.

In an embodiment, the polymer is purified by a process comprising at least one of the following steps:
a. dialysis;
b. ultrafiltration;
c. free protein removal by precipitation, preferably by heat treatment at 60-120° C. or autoclaving, or by the addition of trichloroacetic acid, followed by centrifugation, or by the addition of proteases;
d. nucleic acid removal, by the addition of nucleases.

In an embodiment, the process is characterized in that it is applied to the production of a galactose-rich polymer.

In an embodiment, the process is characterized in that it results in the co-production of polyhydroxyalkanoates, simultaneously with the production of the galactose-rich polymer.

The present invention also provides use of the galactose-rich polymer, characterized in that it is applied to the development of biodegradable films with low gas permeability, namely to carbon dioxide and oxygen.

In an embodiment, the use is characterized in that it is used for the preparation of biodegradable films blended with other biodegradable polymers, such as starch, pectin, alginate, carrageenan, gluten, gellan, Guar gum, pullulan, polyhydroxyalkanoates and chitosan.

In an embodiment, the use is characterized in that it is used for the preparation of biodegradable films, adding one or more plasticizers, such as glycerol, poliethilenglycol, sorbitol, xylitol and lipids.

In an embodiment, the use is characterized in that it is applied as thickener, stabilizer and binding agent for food industry.

In an embodiment, the use is characterized in that it is applied as a source of saccharides, oligosaccharides or low molecular weight polysaccharides, obtained by degradation or derivatization of the original polymer by using physical, chemical, enzymatic and/or biological treatments.

In an embodiment, the use is characterized in that it is applied as a disintegrating, thickening and/or binding agent, in cosmetics and pharmaceuticals.

In an embodiment, the use is characterized in that the polymer is applied to the preparation of microspheres for drug controlled release.

In an embodiment, the use is characterized in that the polymer is applied as flocculating agent namely in mining and food industries.

In an embodiment, the use is characterized in that the polymer is applied as a thickener in the paper industry.

In an embodiment, the use is characterized in that the polymer is applied in explosive industry as binding agent in blasting slurries and waterproof agent in solid explosives (ammonium nitrate and nitro-glycerine, for example).

In an embodiment, the use is characterized in that the polymer is applied in hydromulching, incorporated in the tackifier portion of the slurry used.

In an embodiment, the use is characterized in that the polymer is applied in petroleum industry as suspending agent in well drilling.

In an embodiment, the use is characterized in that the polymer is used as a thickener in textile industry.

In an embodiment, the use is characterized in that the polymer is applied in metallic microparticle coating for medical diagnostic devices.

1. Characterization of the Polymer

This invention concerns a biopolymer whose main component is a high molecular weight (higher than $10^6$) heteropolysaccharide, comprising galactose (50-90%), glucose (1-25%), mannose (1-25%) and rhamnose (0.5-20%). The polysaccharide of the invention may, additionally, contain trace amounts of xylose, ribose, fucose, arabinose and/or fructose. The galactose-rich polymer contains non-sugar components: acyl groups, namely, acetate esters, pyruvate ketals and succinyl half esters; and inorganic residues, namely, phosphate and metal cations. The compositional analysis of the polysaccharide of the invention confirmed the absence of uronic acids and amino sugars.

The physical properties of the polymer of this invention, namely, its solubility and its viscosity in aqueous solution, were compared to other polysaccharides from different origin, namely, plants (Guar gum, Arabic gum and pectin), algae (sodium alginate, k-carrageenan and agar) and bacterial (xanthan gum, from *Xanthomonas campestris*, and gellan gum, from *Sphingomonas paucimobilis*). The results have shown that the polymer of the invention behaves similarly to the different polysaccharides referred, being insoluble in organic compounds (ex. hexane, buthanol, ethyl acetate, chloroform and toluene) and forming viscous aqueous solutions.

Considering its viscosity in aqueous solution, the galactose-rich polymer behaves as a pseudoplastic fluid characterized by a decrease of the viscosity and an increase of the shear stress with increasing shear rates. The viscosity of the polymer's aqueous solution is practically constant in the range pH 3-11, with a partial reduction for lower or higher pH values. This reduction of the solution viscosity is related to a partial degradation of the polymer when subjected to pH values lower than 3 or higher than 11. The viscosity of the polymer's aqueous solutions increases when the temperature is lowered from 100° C. to 4° C. After exposure to high temperatures (80-100° C.) and autoclaving (120° C., 1 bar, for 20 minutes) the galactose-rich polymer keeps its behavior of pseudoplastic fluid.

The galactose-rich polymer solutions show a Newtonian behavior at low shear rates with a zero shear viscosity approaching 5 Pa·s, whereas a shear thinning behavior is observed for shear rates in excess of 1 s$^{-1}$ (FIG. 1). This flow behavior is virtually similar to the one exhibited by the Guar gum solution. In terms of viscosity enhancing properties, the polymer of the invention performs better than both carboxymethyl cellulose and alginate, as the latter show much smaller zero shear viscosities and lesser shear thinning. Conversely, the galactose-rich polymer solution is less viscous than the xanthan solution.

The galactose-rich polymer has both flocculating and emulsifying activities, and has film-forming capacity.

2. Polymer Production 2.1. Microbial Culture

The galactose-rich polymer is obtained by a microbial fermentation process. The microbial culture may be a bacterium belonging to one of the following genera: *Pseudomonas, Klebsiella, Methylobacterium, Erwinia, Alcaligenes, Lactobacillus, Streptoccoccus* or *Ralstonia*. The microbial culture is preferably a *Pseudomonas oleovorans* strain.

The microbial culture may be a wild type microorganism, a variant or a mutant, as long as it possesses the ability to produce the galactose-rich polymer. Alternatively, it may be used a pure culture or a mixed culture of two or more microorganisms, in which, at least one of them is capable of producing the galactose-rich polymer of this invention.

2.2. Culture Medium

The culture medium used in the microbial fermentation consists of a nutrient aqueous medium, containing a carbon source, a nitrogen source and inorganic salts. The carbon source is preferably glycerol or glycerol-rich substrates. Alternatively, the carbon source may be a monomeric, dimeric or olygomeric sugar (ex. glucose, fructose, sucrose, maltose, lactose), an alcohol (ex. methanol, ethanol, manitol, sorbitol), an organic acid (ex. citrate, acetate, malate, succinate, lactate, octanoate), an alkane (ex. hexane, octane) or mixtures therein. The carbon source may also be a food or industrial waste, containing one or more of the compounds referred above, such as, for example, molasses, glycerol-rich product from the biodiesel production, whey or olive-oil production wastes.

The nitrogen source used for the microbial fermentation may be an inorganic salt (ex. ammonium salts, nitrates), organic nitrogen compounds (ex. urea, aminoacids) or mixtures therein or a food or industrial waste containing nitrogen compounds, such as, for example, soya flour, yeast extract, wheat bran or urea.

The culture medium also contains salts comprising the following anions: $SO_4^{2-}$, $Cl^-$, $CO_3^{2-}$, among others. The culture medium also includes trace metals, such as sodium, potassium, calcium, cobalt, manganese, iron and magnesium.

The medium described is merely illustrative of the wide diversity of media that may be used and it should not be considered restrictive.

2.3. Fermentation Conditions

The fermentation process is initiated by the inoculation of the microbial culture in the aqueous nutrient medium described above, under aeration with compressed air. The temperature is controlled between 5 and 75° C., preferably between 26 and 37° C., and the pH is controlled between 4.0 and 9.0, preferably between 6.0 and 7.5. The aeration rate may be kept constant during the fermentation, with values between 0.1 and 2.0 vvm, or it may be allowed to vary between 0 and 2.0 vvm, as a mean of dissolved oxygen concentration control.

At the beginning of the fermentation process, the dissolved oxygen concentration is kept above 80% to promote bacterial cell growth. Concomitant with cell growth, the dissolved oxygen concentration is gradually reduced from its initial value equal or higher that 80% to about 50%. Then, the culture is fed, either by pulses or continuously, with a feeding solution with a composition identical to the culture medium or with a concentration of the carbon source 2-5 times higher. When the culture enters the stationary growth phase and is producing the polymer, the feeding solution may not contain any nitrogen source. As a result, the culture is exposed to conditions of nitrogen limitation (nitrogen concentration null or lower than 0.3 g/L, preferably lower than 0.1 g/L) and carbon availability (carbon concentration between 10 and 100 g/L, preferably between 10 and 20 g/L).

The dissolved oxygen concentration is gradually reduced, concomitant with cell growth, reaching values lower than 30%, being, from that moment on, controlled below 30%, preferably below 10% or even at 0%, by the automatic variation of the mechanical stirring between 0 and 2000 rpm, preferably between 400 and 800 rpm. Within about 10 to 30 hours under these conditions, namely, nitrogen limitation and carbon availability, simultaneously with a dissolved oxygen concentration null or below 10%, there is a sharp increase of the culture broth viscosity, which is related to the galactose-rich polymer production.

The production of the galactose-rich polymer may be kept for a period of 96 to 160 hours of fermentation, depending on the viscosity built up. At some point of the fermentation the culture broth becomes highly viscous and it causes a loss of homogeneity in terms of mixing, mass, oxygen and heat transfer in the bioreactor. The maximum polymer production may vary between 1 and 50 g/L, depending on the culture, the operational conditions and the time of fermentation, as well as the degree of purification of the polymer.

The galactose-rich polymer production process results in the co-production of intracellular biopolymers, namely, polyhydroxyalkanoates that may represent up to 60% of the cell dry weight.

3. Extraction and Purification of the Fermentation Products

At the end of the fermentation, the galactose-rich polymer may be recovered directly from the culture broth, simply by drying at temperatures up to 80° C. or by freeze drying.

Alternatively, the galactose-rich polymer, in its native form, may be precipitated from the culture broth, preferably by the addition of a precipitating agent, that consists of a solvent miscible with water in which the polymer is insoluble, such as, for example, an alcohol (ex. methanol, ethanol, isopropanol) or a ketone (ex. acetone). The galactose-rich polymer is precipitated by the addition of 1 to 5 L of the precipitating agent for each liter of culture broth. The polymer co-precipitates with cells and salts and is dried at temperatures up to 80° C. or freeze dried. Alternatively, the precipitated polymer may be dissolved in water before drying or freeze drying.

In an alternative extraction process, the polymer may be partially purified, by a process that involves cell removal by centrifugation of the culture broth (20000 rpm, 30 minutes), followed by polymer precipitation by the addition of a precipitation agent (1-5 L of precipitating agent for each liter of culture broth). Cell removal is facilitated by the dilution of the culture broth (addition of 1-9 L of deionized water for each liter of culture broth) prior to the centrifugation. The precipitated polymer may be dried at temperatures up to 80° C. or freeze dried, following the precipitation or after dissolution in water.

To obtain a polymer with a higher degree of purity, the polymer is additionally subjected to one or several of the following processes: re-precipitation of the polymer from diluted aqueous solution (less than 1.0 g/L); use of proteolytic enzymes (ex. tripsin) or cell lysing enzymes (ex. lisozyme); addition of protein precipitating agents (ex. trichloroacetic acid) and/or nucleic acids; dialysis, ultrafiltration or diafiltration of aqueous solutions of the polymer. After the purification process, the polymer may be dried at temperatures up to 80° C. or freeze dried, following the precipitation or after dissolution in water.

4. Applications of the Galactose-Rich Polymer

The polymer described in this invention possesses emulsifying and flocculating activities and forms viscous solutions with a stable viscosity under pH, ionic strength and temperature variations. In this way, this polymer is potentially applicable in the same areas as alginate, carrageenan, Guar gum and xanthan gum, such as food and pharmaceutical industries, as well as cosmetics.

The galactose-rich polymer may be used as thickening, binding, gelling, emulsifying, texturing and suspending agent, alone or mixed with other polymers, such as alginate, carrageenan, Guar gum, gellan and xanthan gum, in technical and food applications. Salad dressings, vinegar, ice creams, ketchup, mustard, fruit and vegetable juices, dehydrated products (ex. soups, sauces, cereals) and meat products (ex. sausages and full offes), are examples of food products in which the galactose-rich polymer may be applied.

This polymer may also be used in the paper industry as a thickener, in order to increase the paper surface density and facilitate printing. Similarly to Guar gum, it can enhance sheet formation and increase paper strength.

The galactose-rich polymer may be applied as a binding and disintegrating agent in pharmaceuticals and as a thickener in cosmetic products (ex. tooth paste).

The polymer can be used alone, or blended with other biopolymers, such as starch, pectin, alginate, carrageenan, gluten, gellan and chitosan, in the development of biodegradable films. Since these films have a low permeability to gases (oxygen and carbon dioxide), they may be suitable for packaging materials for specific food products.

Polysaccharides, such as chitosan, starch and Guar gum, have been tested in the preparation of microspheres for drug controlled release. The polymer of this invention may be used as well, alone or mixed with other biopolymers.

Guar gum, a polysaccharide with a chemical composition similar to that of the polymer of this invention, is extensively used in other applications, such as:

Explosives, as binding agent in blasting slurries and water proofing agent in stick explosives (ex. ammonium nitrate and nitro-glycerine).

Petroleum industry, as suspending agent in well drilling.

Hydromulching, incorporated in the tackifier portion of the slurry used.

Textile printing, as thickener for die.

Water treatment and mining industry, as flocculating agent.

The galactose-rich polymer may also be converted into oligosaccharides applying physical treatments (microwave, heating, radiation, sonication), chemical treatments (acid hydrolysis), enzymatic reactions (using microbial enzymes) or by the action of specific microorganisms. The oligosaccharides obtained may have prebiotic properties, which include the stimulation of the microflora in the digestive tract (*Bifidobacteria e Lactobacilli*), as well as the growth inhibition of harmful microorganisms (*Escherichia coli, Clostridium* sp. and *Salmonella*). In addition, these oligosaccharides may possess therapeutic properties, namely prevention of colon cancer and anti-inflammatory action.

EXAMPLES

Example 1

Production of the Galactose-Rich Polymer by *Pseudomonas oleovorans* Fermentation on Glycerol

*Pseudomonas oleovorans* NRRL B-14682 was inoculated in 8 L of nutrient medium with the composition described in Table 1. The bioreactor (Biostat B-plus, Sartorius) was operated under the following conditions: controlled temperature at 30° C.; controlled pH at 6.75-7.00, by automatic addition of NaOH 1M or $H_2SO_4$ 1M; constant aeration rate of 4 slpm (standard liters per minute), corresponding to 0.5 vvm. Concomitant with cell growth, the dissolved oxygen concentration gradually decreased, from 80%, at the beginning of the fermentation, to about 50%, within 20 hours.

From that moment on, the culture started to be continuously fed (about 21 mL/min) with a feeding solution, whose composition was identical to the one described in Table 1, except for the fact that the glycerol concentration was 200 g/L. Thus, the culture was exposed to a condition of nitrogen limitation (ammonium concentration below 0.3 g/L) and carbon availability (glycerol concentration kept higher than 20 g/L).

TABLE 1

| Culture medium composition. | |
|---|---|
| component | concentration |
| Glycerol | 25 g/L |
| $K_2HPO_4$ | 5.8 g/L |

TABLE 1-continued

Culture medium composition.

| component | concentration |
|---|---|
| $KH_2PO_4$ | 3.7 g/L |
| $(NH_4)_2HPO_4$ | 3.3 g/L |
| Trace elements solution[1] | 10 mL |
| $MgSO_4$ 100 mM | 10 mL |

[1]Trace elements solution composition (for 1 L HCl 1N): $FeSO_4 \cdot 7H_2O$, 2.78 g; $MnCl_2 \cdot 4H_2O$, 1.98 g; $CoSO_4 \cdot 7H_2O$, 2.81 g; $CaCl_2 \cdot 2H_2O$, 1.67 g; $CuCl_2 \cdot 2H_2O$, 0.17 g; $ZnSO_4 \cdot 7H_2O$, 0.29 g)

The dissolved oxygen concentration gradually decreased, concomitant with cell growth, until it reached 10% (within 46 hours of fermentation), being, from that moment on, controlled below 10%, by automatic variation of the stirring rate between 400 and 800 rpm. After about 20 hours under these conditions, there was a sharp increase of the culture broth viscosity, which was a consequence of the production of the galactose-rich polymer.

The production of the galactose-rich polymer was maintained up to 96 hours of the fermentation time, when the concentration of the polymer in its native form reached a value of 23 g/L (FIG. 2). By that time, due to the high viscosity, it was no longer possible to maintain the culture broth homogeneous and the fermentation run was terminated.

Example 2

Extraction and Purification of the Galactose-Rich Polymer Produced by *Pseudomonas oleovorans* from Glycerol At the end of fermentation run described in Example 1, the galactose-rich polymer in its native form was precipitated from the culture broth by the addition of ethanol (3 L of ethanol 96% for 1 L of culture broth) the mixture being stored and kept at −20° C. for 1 hour. After that period of time, the precipitated polymer was recovered by centrifugation (10000 rpm, 5 minutes), being a fraction of it dried at 37° C., for 48 hours, and the remaining freeze dried (24 h). The polymer was further purified by dissolution of the dried polymer in deionised water (at a concentration of 1 g/L), centrifuged (20000 rpm, 30 minutes) for cell removal, re-precipitated by the addition of ethanol and, finally, freeze dried.

Example 3

Chemical Analysis of the Galactose-Rich Polymer Produced by *Pseudomonas oleovorans* from Glycerol The glycosyl composition of the polymer obtained by the fermentation process described in Example 1, extracted and purified, as described in Example 2, was performed by combined gas chromatography/mass spectrometry (GC/MS) of the per-O-trimethylsilyl (TMS) derivatives of the monosaccharide methyl glycosides produced from the sample by acidic methanolysis.

Methyl glycosides were first prepared from dry samples by methanolysis in HCl 1M in methanol at 80° C. (18-22 h), followed by re-N-acetylation with pyridine and acetic anhydride in methanol (for detection of amino sugars). The samples were then per-O-trimethylsilylated by treatment with Tri-Sil (Pierce) at 80° C. (0.5 h). GC/MS analysis of the TMS methyl glycosides was performed on an HP 5890 GC interfaced to a 5970 MSD, using an All Tech EC-1 fused silica capillary column (30 m×0.25 mm ID). Inositol was added to the samples before derivatization as an internal standard (20 μg to each sample). The monosaccharides were identified by their retention times in comparison to standards and the carbohydrate character of these are authenticated by their mass spectra. The samples analyzed contained mainly galactose and lower amounts of mannose, glucose and rhamnose, with traces of xylose, ribose and/or fucose.

For glycosyl linkage analysis, the dried samples were permethylated, depolymerized, reduced, and acetylated. The resultant partially methylated alditol acetates (PMAAs) were analyzed by gas chromatography-mass spectrometry (GC-MS). Initially, an aliquot of the samples was permethylated by treatment with sodium hydroxide and methyl iodide in dry DMSO. The permethylation was repeated twice in order to aid complete methylation of the polymer. Following sample workup, the permethylated material was hydrolyzed using 2M trifluoroacetic acid (TFA) (2 h in sealed tube at 121° C.), reduced with $NaBD_4$, and acetylated using acetic anhydride/TFA. The resulting PMAAs were analyzed on a Hewlett Packard 5890 GC interfaced to a 5970 MSD (mass selective detector, electron impact ionization mode); separation was performed on a 30 m Supelco 2330 bonded phase fused silica capillary column. The results obtained showed that the polymer has a high degree of complexity and probably, it is highly ramified. All the monomers were present in the form of piranose rings.

The presence of acyl groups in the galactose-rich polymer was performed by high performance liquid chromatography (HPLC) for the detection of organic acids. Dried samples of the purified polymer were hydrolyzed with TFA 99% (25 μL TFA for 2 mL aqueous solution of the polymer; at 120° C., for 2 h) and analyzed by HPLC, using an Aminex HPX-87H (Biorad) coupled to an UV detector. The mobile phase was $H_2SO_4$ (0.01N), at a flow rate of 0.6 mL/min, at 50° C. Several organic acids were detected, such as pyruvate, acetate and succinate, among others. The content in acyl groups depends on the purification degree of the polymer, decreasing from the native polymer to the semi-purified and to the purified polymer.

Example 4

Measurement of the Viscosity of the Galactose-Rich Polymer Aqueous Solutions Produced by *Pseudomonas oleovorans* from Glycerol The viscosity of the culture broth was measured during the fermentation run described in Example 1 using a Brookfield digital viscometer. From the results obtained it can be concluded that the galactose-rich polymer produced by *Pseudomonas oleovorans* from glycerol originates solutions with a pseudoplastic fluid behaviour (FIG. 3).

The viscosity of 0.5 g/L solutions prepared with purified polymer was measured for different values of pH. The pH of the solution was varied between 2 and 13 by adding an acid (HCl) or a base (NaOH). The viscosity remains practically constant (between 6.0 and 7.0 cps, measured at 12 rpm) in the range of pH 3-11, and shows a decrease only for lower and higher pH values (average value of 2.5 cps for pH2 and for pH13, measured at 12 rpm).

The influence of the temperature on the viscosity was also evaluated. This study was carried out using a 0.5 g/L solution of purified polymer, which was heated and cooled between 4° C. and 100° C. The viscosity of the aqueous solutions gradually increased from 2.2 cps, at 100° C., up to 21.5 cps, at 4° C.

(viscosity measured at 12 rpm). The viscosity at ambient temperature, 20-25° C., was 11.0-13.0 cps (measured at 12 rpm).

Example 5

Preparation of Biodegradable Films Using the Galactose-Rich Polymer Produced by *Pseudomonas oleovorans* from Glycerol The galactose-rich polymer obtained as described in Example 1, was extracted as follows: centrifugation of the culture broth for cell removal, protein precipitation with trichloroacetic acid, TCA, (25 mL of a 100% w/w TCA solution for a total volume of 275 mL) and its separation by centrifugation, and finally, precipitation of the polymer with cold ethanol 96% (1:3) and freeze drying (24 h).

The purified polymer (0.5 g) was dissolved in deionised water (100 mL) under stirring, until a homogeneous solution was formed. A small amount of sodium azide (0.1 g) was added to prevent microbial growth.

The solution was placed under vacuum in order to remove the air bubbles. The mixture was then transferred to a casting container and let to dry at room temperature. The films formed, presenting a 20 to 50±5 μm thickness, had an appearance similar to that of films obtained with other polysaccharides, namely alginate, pectin and carrageenan.

A sample was placed in a desiccator with a relative humidity of 58%, comprising a water content equal to 15.6%. Under these conditions, the Young modulus of the film was of 107 MPa, the strength at break was of 21.2 MPa, the strain at break was 3.6% and the glass transition temperature was 73° C.

REFERENCES

Aucken H M, Wilkinson S G, Pitt T L (1998) *Microbiol*, 144, 639-653.
Bramhachari P V, Dubey S K (2006) *Lett Appl Microbiol*, 43, 571-577.
Bryan B A, Linhardt R J, Daniels L (1986) *Appl Env Microbiol*, 51(6), 1304-1308.
Dermlim W, Prasertsan P, Doelle H (1999) *Appl Microbiol Biotechnol*, 52, 698-703.
D'Haeze W, Glushka J, De Rycke R, Holsters M, Carlson R W (2004) *Mol Microbiol*, 52(2), 485-500.
Eastgate J A (2000) *Mol Plant Pathol*, 1(6), 325-329.
Faber E J, Kamerling J P, Vliegenthart J F G (2001) *Carbohydr Res*, 331, 183-194.
Galindo E, Peña C, Núñez C, Segura D, Espín G (2007) *Microbial Cell Factories*, 6(7), 1-16.
Hung C-C, Santischi P H, Gillow J B (2005) *Carbohydr Pol*, 61, 141-147.
Kim W-S, Schollmeyer M, Nimtz M, Wray V, Geider K (2002) *Microbiology*, 148, 4015-4024.
Lacroix R P, Duncan J R, Jenkins R P, Leitch R A, Perry J A, Richards J C (1993) *Infect Immun*, 61(1), 170-181.
Minogue T D, Carlier A L, Koutsoudis M D, von Bodman S B (2005) *Mol Microbiol*, 56(1), 189-203.
Nagaoka M, Shibata H, Kimura I, Hashimoto S, Kimura K, Sawada H, Yokokura T (1995) *Carbohydr Res*, 274, 245-249.
Nagaoka M, Shibata H, Kimura I, Hashimoto S, Kimura K, Sawada H, Yokokura T (1996) *Carbohydr Res*, 281, 285-291.
Osman S F, Fett W F (1989) *J Bacteriol*, 171(3), 1760-1762.
Pham T H, Webb J S, Rehm B H A (2004) *Microbiology*, 150, 3405-3413.
Ratto M, Verhoef R, Suihko M-L, Blanco A, Schols H A, Voragen A G J, Wilting R, Siika-aho M, Buchert J (2006) *J Ind Biotechnol*, 33, 359-367.
Tavernier P, Portals J, Nava S, Courtois J, Courtois B, Barbotin J (1997) *J Appl Environ Microbiol*, 63(1), 21-26.
Tone-Shimokawa Y, Toida T, Kawashima T (1996) *J Bacteriol*, 178(1), 317-320.
Vanhaverbeke C, Basso C, Colin-Morel P, Gey C, Gamar-Nourani L, Blondeau K, Simonet J-M, Heyraud A (1998) *Carbohydr Res*, 314, 211-220.
Vaningelgem F, Van der Meulen R, Zamfir M, Adriany T, Laws A P, De Vuyst L (2004) *Int Dairy Journal*, 14, 857-864.
Verhoef R, Waard P, Schols H A, Siika-aho M, Voragen A G J (2003) *Carbohydr Res*, 338, 1851-1859.
Verhoef R, Schols H A, Blanco A, Siika-aho M, Ratto M, Buchert J, Lenon G, Voragen A G J (2005) *Biotechnol Bioeng*, 91(1), 91-105.
Whitfield C, Richards J C, Perry M B, Clarke B R, MacLean L L (1991) *J Bacteriol*, 174(15), 4913-4919.
Yang Z (2000) Academic Dissertation, University of Helsinki.
Yang B Y, Brand J, Montgomery R (2001) *Carbohydr Res*, 331, 59-67.

The invention claimed is:

1. A process for the production of galactose-rich polymer comprising, in molar proportion, galactose (50-90%), mannose (1-25%), glucose (1-25%), rhamnose (0.5-20%), and non-sugar components comprising acetate, pyruvate and succinate, the process comprising cultivating at least one *Pseudomonas oleovorans* strain in a microbial culture in which the carbon source comprises,
   a) glycerol or a glycerol-rich substrate;
   b) at least one of the following compounds, mixtures thereof or mixtures thereof with glycerol:
      1) a monomeric, dimeric or olygomeric sugar;
      2) an alcohol;
      3) an organic acid; and
      4) an alkane,
      or
   c) a food or industrial waste comprising at least one of
      1) a monomeric, dimeric or olygomeric sugar;
      2) an alcohol;
      3) an organic acid; and
      4) an alkane
   wherein cultivating the at least one *Pseudomonas oleovorans* strain in the microbial culture comprises:
      i) inoculating the microbial culture in an aqueous nutrient medium, having the carbon source, a nitrogen source and inorganic salts, and aerating the microbial culture to maintain a dissolved oxygen concentration equal to or higher than 80%, while maintaining the pH between 4.0 and 9.0; then
      ii) concomitant with growth of cells of the at least one *Pseudomonas oleovorans* strain, allowing the dissolved oxygen concentration to decrease from equal to or higher than 80% to a level below 50%;
      and when the dissolved oxygen concentration in the culture reaches a level below 50%,
      iii) supplying the microbial culture with a feeding solution consisting of an aqueous nutrient medium comprising the carbon source, the nitrogen source and the inorganic salts, while keeping the carbon source at a concentration between 10 and 100 g/L, and the ammonium of the nitrogen source exhausted or at a concentration below 0.3 g/L in the microbial culture; and iv) allowing the dissolved oxygen concentration in the microbial culture to decrease concomitantly with growth of cells of the at least one *Pseudomonas oleovorans* strain until it reaches a value below 30%; then v) controlling the dissolved oxygen concentration at a level below 30%.

2. The process of claim 1, wherein the *P. oleovorans* strain is NRRL B-14682.

3. The process of claim 1, wherein the microorganism is a variant or a mutant of the *P. oleovorans* NRRL B-14682 strain having all of the essential characteristics of the *P. oleovorans* NRRL B-14682 strain.

4. The process of claim 1, wherein the at least one *Pseudomonas oleovorans* strain is a pure culture, or is a mixed culture comprising several *P. oleovorans* strains that includes NRRL B-14682.

5. The process of obtaining the galactose-rich polymer of claim 1, wherein cultivating the at least one *Pseudomonas oleovorans* strain in the microbial culture comprises:

i) inoculating the microbial culture in a bioreactor in the aqueous nutrient medium, having the carbon source, the nitrogen source and inorganic salts, and aerating the microbial culture to maintain a dissolved oxygen concentration equal or higher than 80%, at a temperature between 26 and 37° C., while maintaining the pH between 6.0 and 7.5, wherein the nitrogen source comprises ammonium; then ii) concomitant with growth of cells of the at least one *Pseudomonas oleovorans* strain, allowing the dissolved oxygen concentration to decrease from equal to or higher than 80% to a level below 50%;

and when the dissolved oxygen concentration in the culture reaches a level below 50%, iii) supplying the microbial culture with a feeding solution consisting of an aqueous nutrient medium comprising the carbon source, the nitrogen source and the inorganic salts, while keeping the carbon source at a concentration between 10 and 20 g/L, and the ammonium of the nitrogen source at a concentration below 0.3 g/L in the microbial culture; and iv) allowing the dissolved oxygen concentration in the microbial culture to decrease in the bioreactor concomitantly with growth of cells of the at least one *Pseudomonas oleovorans* strain until it reaches a value below 30%; then v) controlling the dissolved oxygen concentration in the microbial culture in the bioreactor at a level below 10% while keeping the carbon source at a concentration between 10 and 20 g/L, and the ammonium of the nitrogen source at a concentration below 0.3 g/L in the microbial culture.

6. The process of claim 5, wherein the carbon source is at least one of the following compounds, mixtures thereof or mixtures thereof with glycerol:

1) a monomeric, dimeric or olygomeric sugar which is glucose, fructose, sucrose or lactose;

2) an alcohol that is methanol;

3) an organic acid which iscitrate, acetate, lactate or octanoate; and 4) an alkane which is hexane or octane.

7. The process of claim 5, wherein the carbon source is a food or industrial waste comprising at least one of 1) a monomeric, dimeric or olygomeric sugar;

2) an alcohol;

3) an organic acid; and 4) an alkane, that is molasses, a glycerol-rich product from biodiesel production, or whey or olive-oil production waste.

8. The process of claim 5, wherein the nitrogen source is an inorganic salt, an organic nitrogen compound or a mixture thereof.

9. The process of claim 5, wherein the nitrogen source is food or industrial waste containing nitrogen compounds.

10. The process of claim 9, wherein the food or industrial waste containing nitrogen compounds is soya flour, yeast extract, wheat bran or urea.

11. The process of claim 1, wherein the galactose-rich polymer is directly recovered from the culture, by drying or freeze drying, or alternatively being extracted by a process that comprises sequentially subjecting the culture to the following steps:

i) removing microbial cells from the culture;

ii) precipitating the polysaccharide by the addition of a polar solvent; and iii) separating the precipitated polymer.

12. The process of claim 1, wherein the galactose-rich polymer is purified by a process comprising at least one of the following steps:

a) dialysis;

b) ultrafiltration;

c) free protein removal by precipitation, by
1) heat treatment at 60-120° C.;
2) autoclaving;
3) the addition of trichloroacetic acid, followed by centrifugation; or
4) the addition of proteases, and d) nucleic acid removal, by the addition of nucleases.

13. The process of claim 1, wherein polyhydroxyalkanoates are produced simultaneously with the galactose-rich polymer.

14. The process of claim 1, wherein the pH of the microbial culture is maintained at 6.0 to 7.5 by addition of NaOH or $H_2SO_4$.

15. The process of claim 1, wherein the carbon source is glycerol or a glycerol-rich substrate.

16. The process of claim 1, wherein the carbon source is the food or industrial waste comprising the at least one of 1) a monomeric, dimeric or olygomeric sugar;

2) an alcohol;

3) an organic acid; and 4) an alkane.

* * * * *

UNITED STATES PATENT AND TRADEMARK OFFICE
CERTIFICATE OF CORRECTION

PATENT NO. : 8,679,796 B2  
APPLICATION NO. : 12/595392  
DATED : March 25, 2014  
INVENTOR(S) : Carvalho Fernandes De Miranda Reis et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 938 days.

Signed and Sealed this
Twenty-ninth Day of September, 2015

Michelle K. Lee
*Director of the United States Patent and Trademark Office*